US012558202B2

(12) United States Patent
Lim et al.

(10) Patent No.: US 12,558,202 B2
(45) Date of Patent: Feb. 24, 2026

(54) DENTAL BULK BLOCK AND METHOD OF MANUFACTURING SAME

(71) Applicant: HASS CO., LTD., Gangneung-si (KR)

(72) Inventors: Hyung Bong Lim, Ansan-si (KR); Yong Su Kim, Gangneung-si (KR)

(73) Assignee: HASS CO., LTD, Gangneung-si (KR)

( * ) Notice: Subject to any disclaimer, the term of this patent is extended or adjusted under 35 U.S.C. 154(b) by 916 days.

(21) Appl. No.: 17/518,654

(22) Filed: Nov. 4, 2021

(65) Prior Publication Data

US 2023/0032952 A1 Feb. 2, 2023

(30) Foreign Application Priority Data

Jul. 26, 2021 (KR) ........................ 10-2021-0098063

(51) Int. Cl.
 *A61C 13/00* (2006.01)
 *A61K 6/17* (2020.01)
 *A61K 6/833* (2020.01)

(52) U.S. Cl.
 CPC ............ *A61C 13/0022* (2013.01); *A61K 6/17* (2020.01); *A61K 6/833* (2020.01)

(58) Field of Classification Search
 CPC ....... A61C 13/0022; A61K 6/17; A61K 6/833
 See application file for complete search history.

(56) References Cited

U.S. PATENT DOCUMENTS 3,882,600 A * 5/1975 Plymale ................... A61K 6/76
 264/269
5,057,018 A 10/1991 Bowen
2014/0141960 A1 * 5/2014 Borczuch-Laczka ........................
 C03C 23/0005
 501/63

FOREIGN PATENT DOCUMENTS

| CN | 106365456 | B | 6/2019 |
| CN | 111018356 | A | 4/2020 |
| EP | 0779612 | A1 | 6/1997 |
| EP | 3372568 | A1 | 9/2018 |
| EP | 3744696 | A1 | 12/2020 |
| JP | 2014515722 | A | 7/2014 |
| JP | 2019-531241 | A | 10/2019 |
| JP | 2020193191 | A | 12/2020 |
| KR | 10-2014-0125798 | A | 10/2014 |
| KR | 10-2015-0137573 | A | 12/2015 |

(Continued)

OTHER PUBLICATIONS https://www.studocu.com/in/document/kerala-university-of-health-sciences/pharmacy/crystallinity/65547864 accessed Mar. 25, 2025 (Year: 2025).*

(Continued)

*Primary Examiner* — Cameron K Miller
(74) *Attorney, Agent, or Firm* — NKL Law; Jae Youn Kim

(57) ABSTRACT

Provided is a dental bulk block made from a glass-ceramic material having a crystalline phase embedded in an amorphous glass matrix. The crystalline phase includes eucryptite and at least one lithium silicate-based crystalline phase selected from the group consisting of lithium metasilicate and lithium disilicate. The dental bulk block is a functionally graded material having a crystalline size gradient with respect to a depth thereof and having no interface at a point of change in main crystalline size gradient value. The bulk block that is heat-treated at 820° C. for 40 minutes exhibits a characteristic peak of a spodumene crystalline phase in an X-ray diffraction analysis result graph unlike the bulk block that is heat-treated at 820° C. for 2 minutes.

8 Claims, 10 Drawing Sheets as-machined$(SiO_2/Li_2O=2.20\sim2.59)$

○ : $Li_2O \cdot SiO_2$
● : $Li_2O \cdot 2SiO_2$
◇ : $Li_2O \cdot Al_2O_3 \cdot 2SiO_2$
◆ : $Li_2O \cdot Al_2O_3 \cdot 4SiO_2$

(56)          References Cited

FOREIGN PATENT DOCUMENTS

| KR | 10-2018-0102711 | A | 9/2018 |
| KR | 10-2020-0137198 | A | 12/2020 |
| KR | 10-2246195 | B1 | 4/2021 |

OTHER PUBLICATIONS

Jung, Seok Ki et al., "Modulation of Lithium Disilicate Translucency through Heat Treatment", Materials, Apr. 21, 2021, 14, Article No. 2094, pp. 1-10, Seoul, Republic of Korea.

* cited by examiner

Cutting resistance(%)

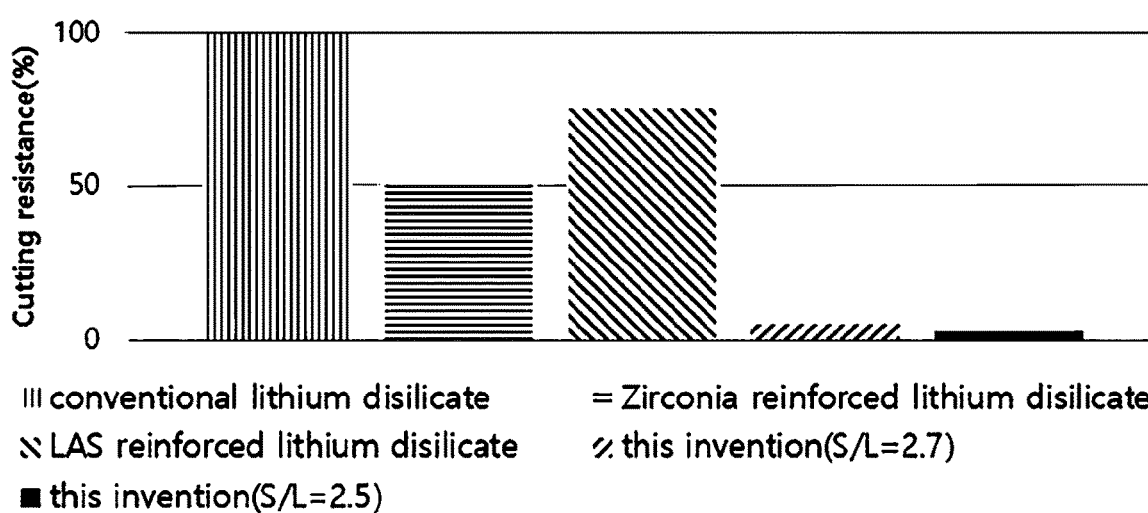

III conventional lithium disilicate
≈ LAS reinforced lithium disilicate
■ this invention(S/L=2.5)

= Zirconia reinforced lithium disilicate
⁒ this invention(S/L=2.7)

FIG. 5

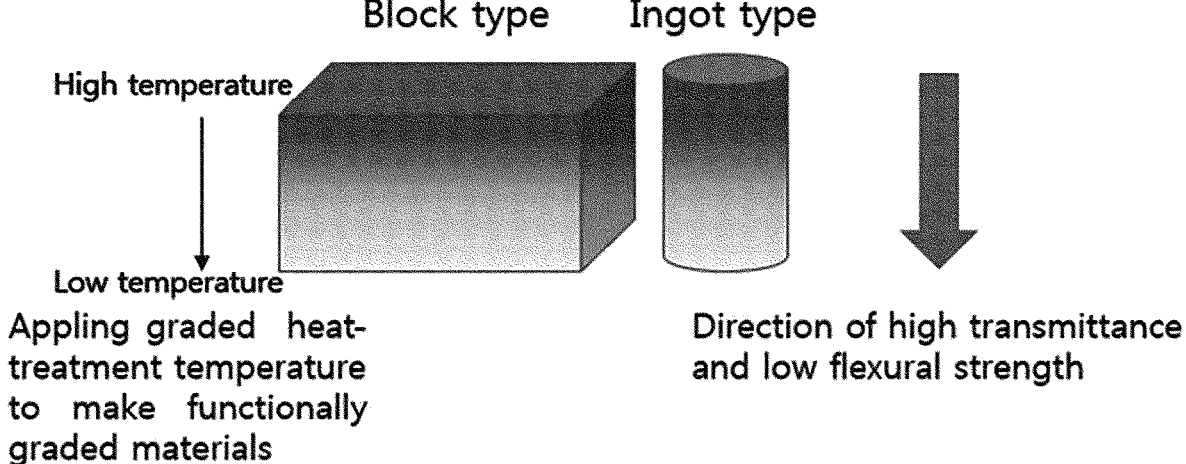

Block type        Ingot type

High temperature

Low temperature

Appling graded heat-treatment temperature to make functionally graded materials

Direction of high transmittance and low flexural strength

FIG. 6

DENTAL BULK BLOCK AND METHOD OF MANUFACTURING SAME

CROSS REFERENCE TO RELATED APPLICATION

The present application claims priority to Korean Patent Application No. 10-2021-0098063, filed Jul. 26, 2021, the entire contents of which is incorporated herein for all purposes by this reference.

BACKGROUND OF THE INVENTION

Field of the Invention

The present disclosure relates generally to a dental bulk block useful for manufacturing artificial teeth having structural characteristics similar to those of natural teeth. More particularly, the present disclosure relates to a dental bulk block with improved machinability, and a method of manufacturing the same.

Description of the Related Art

Crown materials refer to prosthetic materials for restoration of dentin and enamel of damaged teeth. The crown materials may be classified into inlays, onlays, veneers, and crowns depending on the application site. Since the crown materials are applied to the outer surfaces of teeth, high aesthetic properties are required. Also, high strength is required to withstand abrasion against antagonistic teeth or fractures such as chipping. Common crown materials include leucite glass-ceramics, reinforced porcelain, and fluorapatite $(Ca_5(PO_4)_3F)$ glass-ceramics. Despite of high aesthetic properties thereof, these crown materials are vulnerable to fractures due to having a low strength of about 80 to 120 MPa. Therefore, research is currently being conducted to develop various high-strength crown materials.

Lithium silicate glass-ceramics were introduced by Marcus P. Borom and Anna M. Turkalo (The Pacific Coast Regional Meeting, The American Ceramic Society, San Francisco, CA, Oct. 31, 1973 (Glass division, No. 3-G-73P)) in 1973.

They studied the formation of various crystal nuclei, and the crystalline phases and strengths according to different growth heat-treatment conditions using $Li_2O$—$Al_2O_3$—$SiO_2$—$Li_2O$—$K_2O$—$B_2O_3$—$P_2O_5$-based glass. A high-temperature lithium disilicate crystalline phase formed from low-temperature lithium metasilicate exhibited a strength of 30 to 35 KPS, which is due to the residual stress caused by the difference in coefficient of thermal expansion between base glass, mother glass, $Li_2SiO_5$, and $Li_2SiO_3$ phases.

Materials and methods for manufacturing artificial teeth using glass containing a lithium disilicate crystal (monolithic dental crown) are already known through various patents. However, in the known techniques, it is difficult to perform direct machining due to due to a coarse crystalline phase. For machining, it is necessary to primarily form a lithium metasilicate crystalline phase (machinable crystalline), and then secondarily form a high-strength lithium disilicate crystalline phase through heat treatment. Therefore, dimensional accuracy is lowered due to shrinkage caused by the heat treatment, and it is cumbersome to additionally perform the heat treatment. In general, prosthetic machining by CAD-CAM requires manufacturing of a prosthesis by directly machining a bulk body in a dental clinic, and fitting of the bulk body to a patient as quickly as possible (one-day appointment). Therefore, a time delay due to a heat treatment process poses financial difficulties on patients.

In addition, a conventional lithium disilicate glass-ceramic material has a limit in realizing high light transmittance or opalescence similar to those of natural teeth due to its coarse crystalline phase.

In particular, in order to machine the conventional lithium disilicate glass-ceramic material, a lithium metasilicate glass-ceramic having good machinability is primarily prepared, and then lithium disilicate is prepared through a secondary crystallization heat treatment to improve strength. In this case, the size of a crystalline phase is about equal to or greater than 3 μm. However, in this state, machinability is remarkably lowered, and only the required strength can be realized.

In an effort to solve these problems, the present applicant has proposed a method of manufacturing a glass-ceramic including lithium disilicate and silicate crystalline phases with excellent machinability by changing a primary heat treatment temperature so as to control a crystal size, and has received a patent therefor (Korean Patent No. 10-1975548) Specifically, there has been disclosed a method of manufacturing a glass-ceramic for teeth, the glass-ceramic including a silica crystalline phase. The method includes the steps of: performing a primary heat treatment on a glass composition at 400 to 850° C., the glass composition including 60 to 83 wt % of $SiO_2$, 10 to 15 wt % of $Li_2O$, 2 to 6 wt % of $P_2O_5$, which serves as a nucleating agent, 1 to 5 wt % of $Al_2O_3$, which increases the glass transition temperature and softening point and improves the chemical durability of glass, 0.1 to 3 wt % of SrO, which increases the softening point of glass, 0.1 to 2 wt % of ZnO, 1 to 5 wt % of a colorant, and 2.5 to 6 wt % of $Na_2O+K_2O$, which is an alkali metal oxide that increases the coefficient of thermal expansion of glass; and performing a secondary heat treatment at 780 to 880° C. after the primary heat treatment. The primary heat treatment results in the generation of a lithium disilicate crystalline phase and a silica crystalline phase each having a nano size of 5 to 2,000 nm, and the secondary heat-treatment temperature is used to control light transmittance.

Meanwhile, the improvement in standard of living has increased the demand for aesthetics in the field of dentistry. In response to patient needs for aesthetics, various research on aesthetic prosthetic restorations using various materials is being conducted.

Examples of factors affecting the aesthetics of porcelain restorations as main aesthetic restorative materials that are currently used include the appearance of teeth, surface condition, transparency, color tone, etc. Of these, transparency is a particularly important factor for successfully manufacturing restorations. Although a lot of research and development on the mechanical and physical properties of porcelain for aesthetic prosthesis has been conducted, there still exist a lot of problems associated with matching of colors. In addition, from a clinical and technical point of view, there exist a lot of difficulties associated with the selection of the color of restorations, especially transparency.

In aesthetic prosthodontics, examples of factors affecting aesthetics during dental restoration include color, the shape and size of teeth, the arrangement and ratio of teeth, light beams, transmittance, and the design of restorations. In daily life, people are very perceptive to teeth color and shape.

A natural tooth has parts that have different colors from the cervical to the incisal areas.

In view of this, recently, a method of manufacturing artificial teeth that can imitate the deep color of natural teeth using a so-called build-up method has also been known.

The build-up method refers to a method of stacking layers of powder such as porcelain or zirconia to form a colored artificial tooth, and then heat-treating the artificial tooth to realize layers having colors similar to those of a natural tooth. Although it is possible to imitate the color of natural teeth quite similarly, the aesthetics of artificial teeth are determined entirely according to the skill of the technician. Therefore, the build-up method is problematic in that reproducibility is low, it is impossible to directly manufacture artificial teeth, which is not advantageous to the patient, and it is difficult to realize an artificial tooth by cutting machining such as CAD/CAM machining.

Meanwhile, in the case of manufacturing artificial teeth by cutting machining such as CAD/CAM machining using a conventional bulk block, the bulk block is composed of materials exhibiting uniform physical properties. Therefore, unlike the natural tooth, it is inevitable to obtain an artificial tooth having a single color. In particular, the artificial tooth thus obtained has a heterogeneous appearance when applied to the front tooth, etc., which inevitably causes the problem of deteriorated naturalness.

Controlling the transparency and machinability is possible through the secondary heat treatment using the above-described method of manufacturing the glass-ceramic described in Korean Patent No. 10-1975548 granted to the present applicant. However, in the case of the glass-ceramic thus obtained, a single block has uniform physical properties. Therefore, in order to realize a deep color as in a natural tooth using the obtained glass-ceramic, it is necessary to apply a method of combining a plurality of resultant products. In other words, it is not easy to immediately realize natural-colored teeth by directly subjecting the bulk block itself to cutting machining such as CAD/CAM machining.

In an effort to solve these problems, the present applicant has proposed a bulk block that is useful for manufacturing an artificial tooth prosthesis similar to a natural tooth, and not only shortens the time and processes required to manufacture an artificial tooth prosthesis, but also increases the structural stability in terms of force distribution through functional grading of mechanical properties, and received a patent therefor (Korean Patent No. 10-2246195).

The present disclosure has been devised to provide a gradient bulk block with improved aesthetics and, in particular, improved machinability.

The foregoing is intended merely to aid in the understanding of the background of the present disclosure, and is not intended to mean that the present disclosure falls within the purview of the related art that is already known to those skilled in the art.

SUMMARY OF THE INVENTION

Accordingly, the present disclosure has been made keeping in mind the above problems occurring in the related art, and an objective of the present disclosure is to provide a dental bulk block which is used to manufacture an artificial tooth restoration exhibiting multi-gradation of light transmittance or physical properties similar to those of natural teeth so as to have reproducibility through cutting machining such as CAD/CAM machining without requiring the addition of any other process.

Another objective of the present disclosure is to provide a dental bulk block with improved machinability, dental bulk block being capable of not only shortening the time and processes required to manufacture an artificial tooth prosthesis, but also increasing the structural stability in terms of force distribution through functional grading of mechanical properties.

Still another objective of the present disclosure is to provide a method of easily manufacturing a dental bulk block which is used to manufacture an artificial tooth restoration exhibiting multi-gradation of transmittance or physical properties similar to those of natural teeth.

Still another objective of the present disclosure is to provide a method of easily manufacturing such a dental bulk block into a dental restoration using a machining machine-tool.

In order to achieve the above objectives, one embodiment of the present invention provides a dental bulk block comprising a crystalline phase in an amorphous glass matrix. The crystalline phase may include eucryptite and at least one lithium silicate-based crystalline phase selected from the group consisting of lithium metasilicate and lithium disilicate. The dental bulk block may be a functionally graded material having a crystalline size gradient with respect to the depth thereof and having no interface at the point of change in crystalline size gradient value. The bulk block that is heat-treated at 820° C. for 40 minutes may exhibit a characteristic peak of a spodumene crystalline phase in an X-ray diffraction analysis result graph unlike the bulk block that is heat-treated at 820° C. for 2 minutes.

In a preferred embodiment, the crystalline size gradient may be sloped such that the lithium silicate-based crystalline phase has a mean grain size in the rage of 0.05 to 1.0 $\mu$m, and the eucryptite crystalline phase has a mean grain size in the range of 1.0 to 4.0 $\mu$m.

In a preferred embodiment, the dental bulk block may have a light transmittance gradient with respect to the depth thereof.

In a preferred embodiment, the light transmittance gradient may be in a range of 25 to 40% based on a wavelength of 550 nm.

In a preferred embodiment, the light transmittance gradient may vary even in a range of 0.5 mm in depth.

In a preferred embodiment, the dental bulk block may have a gradient in L*, a*, and b* values measured by color difference analysis, and a color difference value ($\Delta$E) may vary even in a range of 1.5 mm in depth.

In a preferred embodiment, the dental bulk block may have a crystallinity degree of 40 to 70%.

In a preferred embodiment, the crystalline phase may include 40 to 60 vol. % of the lithium silicate-based crystalline phase, and 40 to 60 vol. % of the eucryptite crystalline phase, based on the total volume of the crystalline phases.

In a preferred embodiment, the dental bulk block may have a flexural strength gradient with respect to the depth thereof.

In a preferred embodiment, the flexural strength gradient may be in a range of 220 to 350 MPa. In a preferred embodiment, the dental bulk block may include a continuous glass matrix.

In a preferred embodiment, the glass matrix may include 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$, and in which the molar ratio of $SiO_2/(Li_2O+Al_2O_3)$ may be 2.10 to 2.90. Specifically, when the lithium silicate-based crystalline phase includes both lithium metasilicate and lithium disilicate, the molar ratio of $SiO_2/Li_2O$ in the glass matrix may be 2.20 to 2.59. On the other hand, when the lithium silicate-based crystalline phase includes only lithium disilicate, the molar ratio of $SiO_2/Li_2O$ in the glass matrix may be 2.60 to 3.00.

Another aspect of the present disclosure provides a method of manufacturing a dental bulk block, the method including the steps of: preparing a block having a predetermined shape by melting a glass composition including 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$, in which the molar ratio of $SiO_2/(Li_2O+Al_2O_3)$ is 2.10 to 2.90, followed by molding and cooling of the melted glass composition in a mold, followed by annealing from 480° C. down to 250° C. at a predetermined rate for a period of 20 minutes to 2 hours; and heat-treating the block in a gradient heat treatment furnace at a temperature in the range of 850 to 1,000° C. under a temperature gradient in a depth direction of the block.

Specifically, when a lithium silicate-based crystalline phase includes both lithium metasilicate and lithium disilicate, the molar ratio of $SiO_2/Li_2O$ in the glass composition may be 2.20 to 2.59.

On the other hand, when the lithium silicate-based crystalline phase includes only lithium disilicate, the molar ratio of $SiO_2/Li_2O$ in the glass composition may be 2.60 to 3.00.

In a preferred embodiment, the heat-treating of the block may be performed under conditions in which the temperature is raised to a maximum temperature at a temperature increase rate of 30 to 110° C./min, and the maximum temperature is maintained for 1 to 5 minutes.

Still another aspect of the present disclosure provides a method of manufacturing a dental restoration, the method including the steps of manufacturing: a predetermined dental restoration by machining the above-described dental bulk block using a machining machine-tool; and polishing or glazing the predetermined dental restoration.

In a preferred embodiment, the glazing may be performed at a temperature in a range of 730 to 820° C. for 30 seconds to 10 minutes.

In a preferred embodiment, the glazing may be performed so that the dental restoration has a biaxial flexural strength gradient of 300 to 380 MPa.

In a preferred embodiment, the glazing may be performed to control the light transmittance of the machined dental restoration through heat treatment at a temperature of at least 825° C.

In a preferred embodiment, the glazing may be performed at a temperature of at least 825° C. for 1 to 10 minutes. Specifically, the glazing may be performed so that the dental restoration has a biaxial flexural strength gradient of 350 to 400 MPa.

The dental bulk block according to the present disclosure can be used to manufacture an artificial tooth restoration exhibiting multi-gradation of light transmittance or physical properties similar to those of natural teeth so as to have reproducibility through cutting machining such as CAD/CAM machining without requiring the addition of any other process. In addition, the dental bulk block can not only shorten the time and processes required to manufacture an artificial tooth prosthesis, but also increase the structural stability in terms of force distribution through functional grading of mechanical properties. The dental bulk block can be manufactured through a facile method of performing gradient heat treatment using a single glass composition having a specific composition.

BRIEF DESCRIPTION OF THE DRAWINGS

FIGS. 1A and 1B each illustrates a graph of an X-ray diffraction (XRD) analysis result of a dental bulk block according to an embodiment of the present disclosure, in which FIG. 1A illustrates a block in which the molar ratio of $SiO_2/Li_2O$ is 2.20 to 2.59, and FIG. 1B illustrates a block in which the molar ratio of $SiO_2/Li_2O$ is 2.60 to 3.00;

FIGS. 2A and 2B illustrate graphs of X-ray diffraction (XRD) analysis results of comparing the case of heat-treating the bulk block according to the present invention at 820° C. for 40 minutes with the case of heat-treating the bulk block at 820° C. for 2 minutes to confirm a characteristic peak of a spodumene ($Li_2O·Al_2O_3·4SiO_2$) crystalline phase, in which FIG. 2A illustrates a graph of an X-ray diffraction (XRD) analysis result of the block heat-treated at 820° C. for 2 minutes, which is a condition for glazing of typical dental prostheses, and FIG. 2B illustrates a graph of an X-ray diffraction (XRD) analysis result of the block heat-treated at 820° C. for 40 minutes, which is a condition experimentally set for the identification of the crystalline phase in the present invention;

FIG. 5 is a comparative graph of cutting resistance for the bulk block according to the present invention;

FIG. 6 is a mimetic diagram illustrating a method of manufacturing a dental bulk block according to an embodiment of the present invention;

FIGS. 8A and 8B are graphs each illustrating a change in biaxial flexure strength as a function of the depth of the bulk block according to the embodiment of the present invention depending on glazing temperature conditions, in which FIG. 8A illustrates a result of glazing the bulk block at 820° C. for 2 minutes, and FIG. 8B illustrates a result of glazing the bulk block at 840° C. for 2 minutes.

DETAILED DESCRIPTION OF THE INVENTION

Figure 1A:
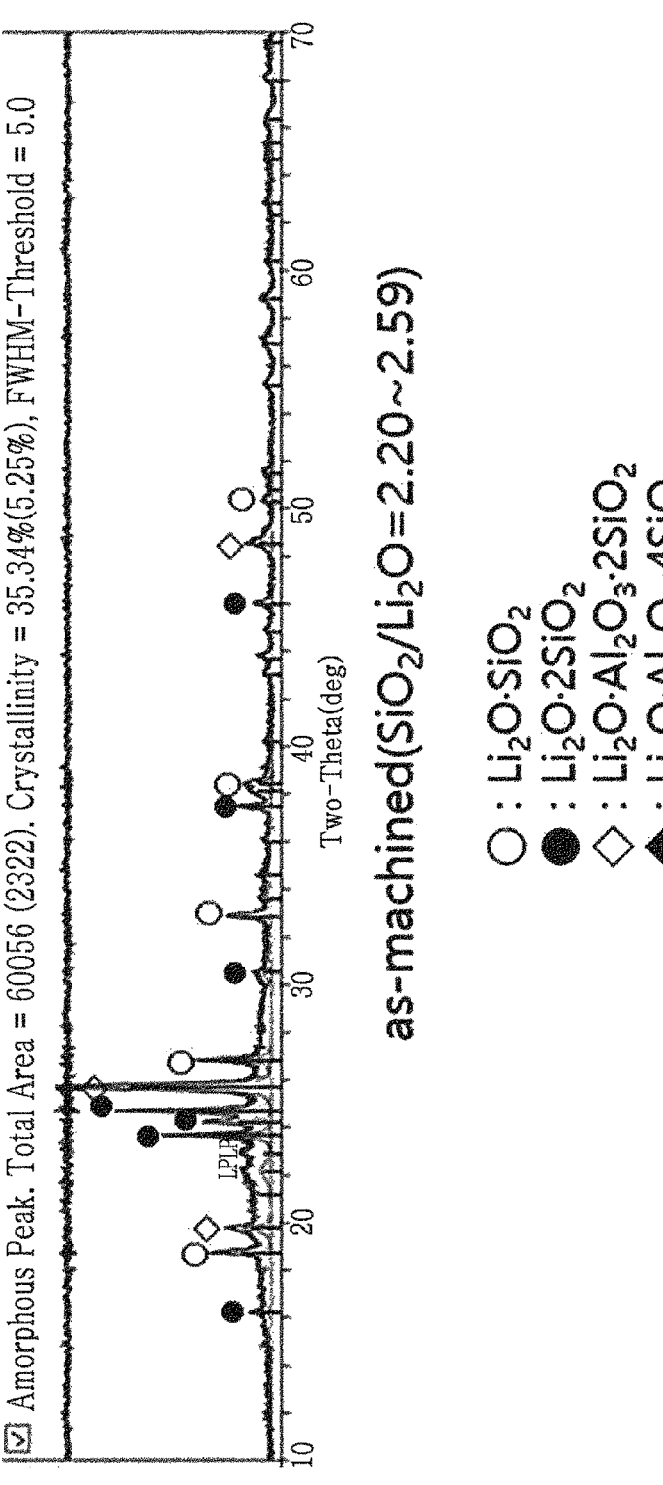

The foregoing and further aspects of the present disclosure will become more apparent from exemplary embodiments in conjunction with the accompanying drawings. Hereinafter, exemplary embodiments of the present disclosure will be described in detail such that the disclosure can be better understood and easily embodied by one of ordinary skill in the art to which this disclosure belongs.

One embodiment of the present invention provides a dental bulk block comprising a crystalline phase in an amorphous glass matrix. The crystalline phase may include eucryptite and at least one lithium silicate-based crystalline phase selected from the group consisting of lithium metasilicate and lithium disilicate. The dental bulk block is a functionally graded material having a crystalline size gradient with respect to the depth thereof and having no interface at the point of change in crystalline size gradient value. The bulk block that is heat-treated at 820° C. for 40 minutes exhibits a characteristic peak identified as a spodumene crystalline phase unlike the bulk block that is heat-treated at 820° C. for 2 minutes, which is confirmed through results of X-ray diffraction (XRD) analysis.

This feature is due to the fact that the phase transformation from eucryptite to spodumene occurs as a result of the movement of Si ions attributable to an increase in heat treatment time.

In the previous and following descriptions, the meaning "having a crystalline size gradient with respect to the depth" means that a gradient of change in size of the crystalline phase exists when graphing the size of the crystalline phase depending on the depth of the bulk block. That is, this means that the size of the crystalline phase is expressed in a gradation form with respect to the depth of the bulk block.

Furthermore, the meaning "point of change in crystalline size gradient value" means a point at which the gradient value of change in the size of the crystalline phase is substantially changed when graphing the size of the crystalline phase depending on the depth of the bulk block. Here, the meaning "substantially changed" may mean a change in a single numerical value, and may also include a substantial change in the distribution of the value.

Furthermore, the meaning "having no interface at the point of change in crystalline size gradient value" may be interpreted to mean that in the case of the same crystalline phase, no significant interface indicating interlayer separation exists at the depth point of the bulk block at which the crystalline size gradient is changed. That is, the bulk block has a crystalline size gradient in a continuous form without any depth-dependent interface.

Meanwhile, the "functionally graded material (FGM)" generally refers to a material in which the properties of a constituent material continuously varies across its interface. In the present disclosure, although substantially no interface exists, the expression of the functionally graded material is borrowed in terms of continuously varying the properties of the constituent material.

In the previous and following descriptions, the bulk block is not limited in shape, and for example, may include a bulk body of various types such as a block type, a disk type, an ingot type, a cylinder type, etc.

The bulk block according to the present invention includes eucryptite and at least one lithium silicate-based crystalline phase selected from the group consisting of lithium metasilicate and lithium disilicate. The bulk block may include lithium phosphate as an additional crystalline phase.

Figure 1B:
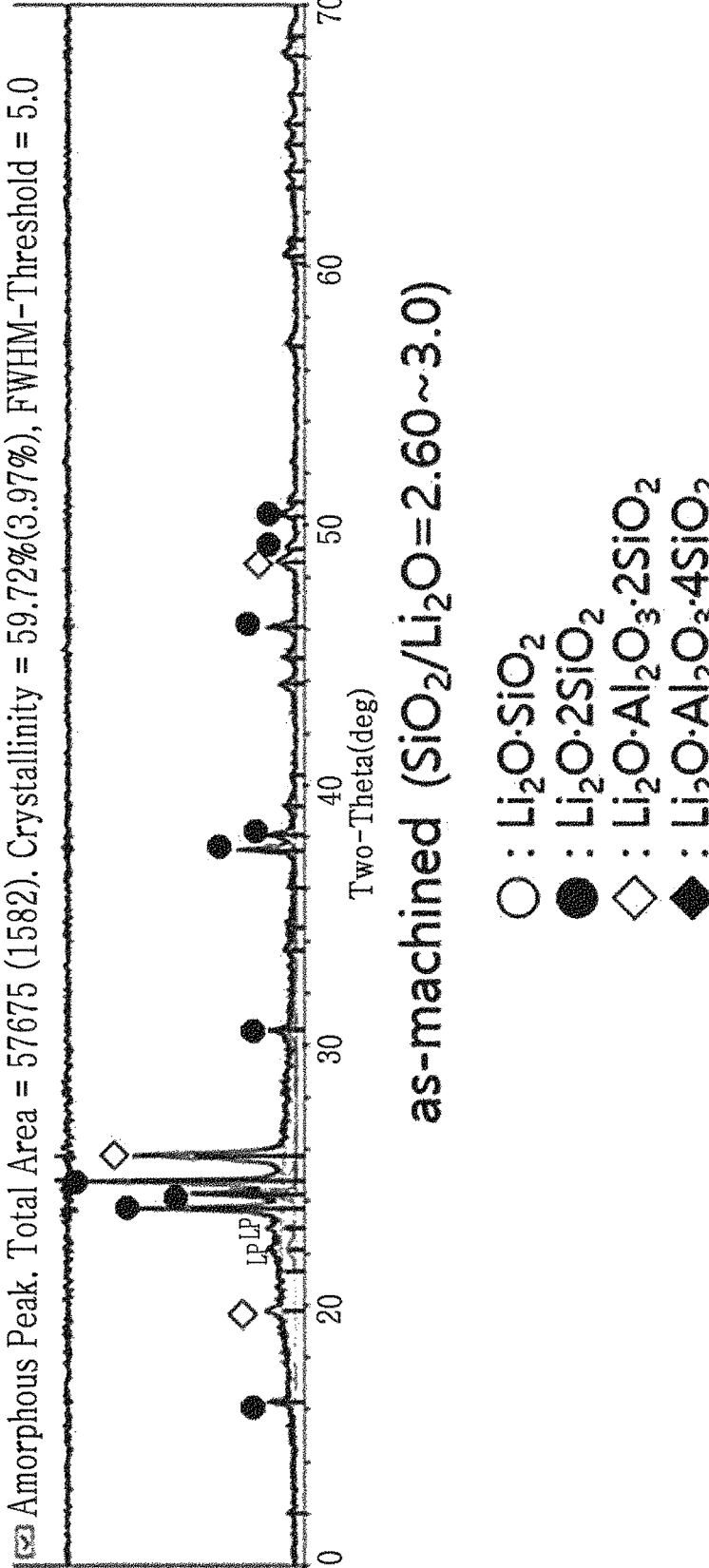

FIGS. 1A and 1B each illustrates a graph of an X-ray diffraction (XRD) analysis result of a dental bulk block according to an embodiment.

FIG. 1A illustrates a bulk block including both lithium metasilicate and lithium disilicate as a lithium silicate-based crystalline phase and eucryptite as another crystalline phase, and FIG. 1B illustrates a bulk block including only lithium disilicate as a lithium silicate-based crystalline phase and eucryptite as another crystalline phase.

Referring to FIGS. 1A and 1B, the dental bulk block according to the embodiment of the present disclosure includes a lithium metasilicate or lithium disilicate crystalline phase, and a main peak appears at $2\theta=19.7, 25.7, 48.5$ (degrees), etc., which may be interpreted as beta-eucryptite (JCPDS #12-0709).

In the dental bulk block according to the embodiment of the present disclosure disclosed herein, as the additional sub-crystalline phase in addition to eucryptite, a main peak appears at $2\theta=22.18$ and $22.9$ (degrees), which may be interpreted as lithium phosphate (main peak at $2\theta=22.3$ and $23.1$).

In the previous and following descriptions, XRD analysis will be understood to mean an analysis that is based on a result obtained using an X-ray diffraction analyzer (D/MAX-2500, Rigaku, Japan; Cu Kα (40 kV, 60 mA), scan rate: 6°/min., 2θ: 10 to 60 (degrees)).

Eucryptite is a lithium aluminum silicate-based (which may be abbreviated as LAS) crystalline phase represented by the chemical formula $LiAlSiO_4$, and has a property of low cutting resistance against machining tools due to residual thermal stress compared to other LAS-based crystalline phase such as spodumene ($LiAlSi_2O_6$), orthoclase ($LiAlSi_3O_8$), petalite ($LiAlSi_4O_8$) or virgilite ($LiAlSi_5O_{12}$). When the bulk block includes such a crystalline phase, a lower tool wear rate may be exhibited than when only lithium disilicate exists. Therefore, lowered tool resistance results in improved cutting efficiency, minimized milling tool consumption, and minimized chipping (tearing and breaking off) generated during machining.

The dental bulk block according to the embodiment of the present invention is featured in that when the bulk block that is heat-treated at 820° C. for 40 minutes exhibits a characteristic peak identified as the spodumene crystalline phase in an XRD analysis result graph unlike the bulk block that is heat-treated at 820° C. for 2 minutes. Under the same heat treatment temperature condition of 820° C., in the case of heat-treating the bulk block for 2 minutes, there is no significant change in the composition of the crystalline phase. However, in the case of heat-treating the bulk block for 40 minutes, as the movement of $SiO_2$ in the glass matrix becomes efficient, eucryptite, a LAS-based crystalline phase with a low $SiO_2$ amount, undergoes a phase transformation to spodumene, a LAS-based crystalline phase with an increased $SiO_2$ amount.

In the previous and following descriptions, the meaning that a block is heat-treated at 820° C. specifically means that a bulk block with dimensions of 10×10×1.5 mm is heated in a dental porcelain furnace (CS, manufactured by Ivoclar vivadent) to a maximum temperature of 820° C. at a temperature increase rate of 45° C./min. The heat treatment time of 40 minutes means that the holding time is 40 minutes under the maximum temperature, and the heat treatment time of 2 minutes means that the holding time is 2 minutes under the maximum temperature.

Such a feature of the present invention can be understood to be due to the fact that as the heat treatment time increases from 2 minutes to 40 minutes at the maximum heat treatment temperature, Si ions in the glass matrix move more actively and farther, leading to a phase transformation of eucryptite ($LiAlSiO_4$) to spodumene ($LiAlSi_2O_6$) containing more $SiO_2$. This feature can also be understood to prove that the dental bulk block according to the present invention includes eucryptite as a crystalline phase.

Figure 2A:
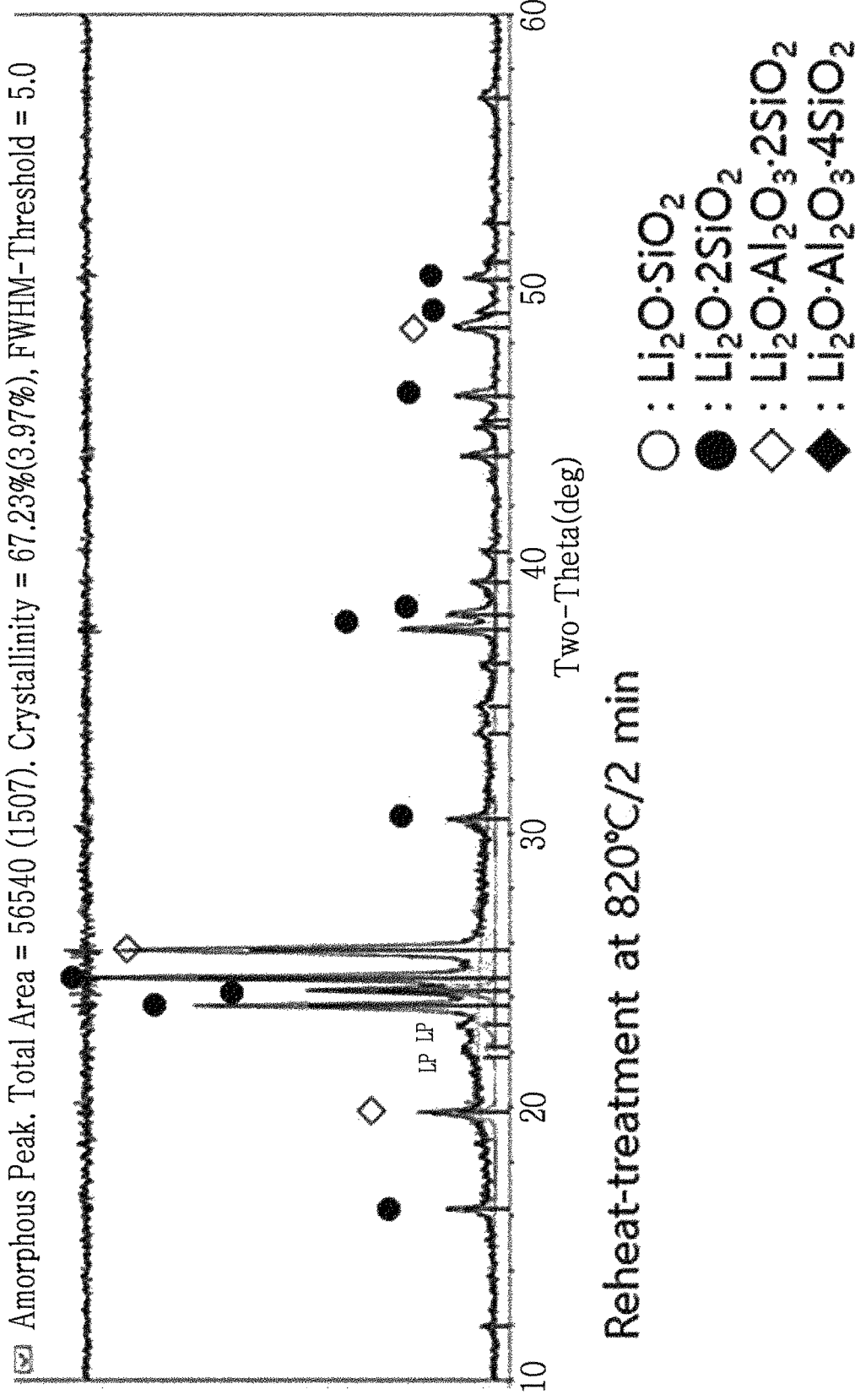
Figure 2B:
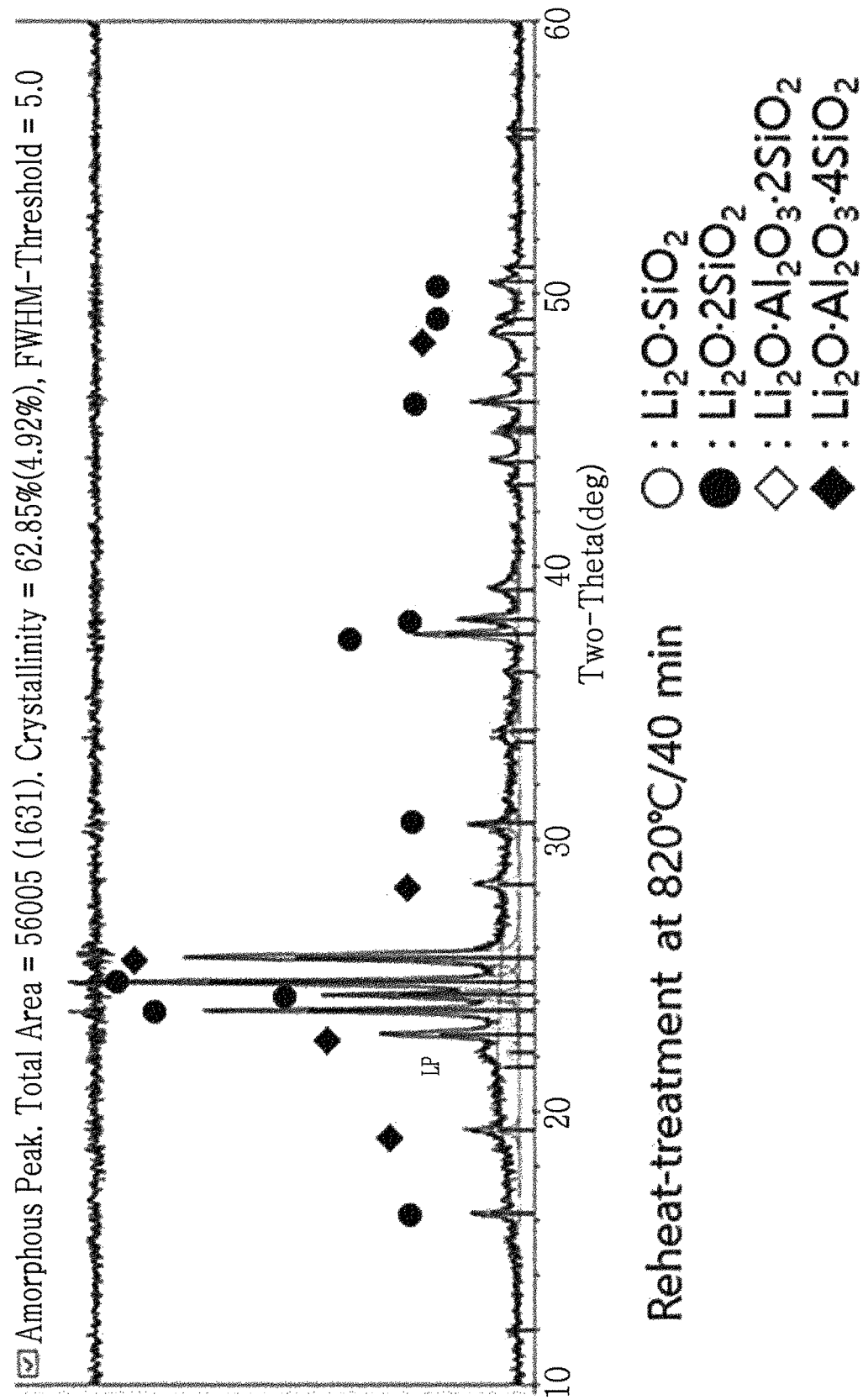

This can be confirmed by the graphs of FIGS. 2A and 2B illustrating the results of XRD analysis. FIG. 2A illustrates a result of heat-treating the bulk block (specifically, the bulk block illustrated in FIG. 1A or 1B) according to the embodiment of the present invention at 820° C. for 2 minutes, and FIG. 2B illustrates a result of heat-treating the bulk block (specifically, the bulk block illustrated in FIG. 1A or 1B) according to the embodiment of the present invention at 820° C. for 40 minutes.

In the case of the graph illustrated in FIG. 2B, it can be seen that unlike the graph illustrated in FIG. 2A, a characteristic peak identified as a spodumene crystalline phase appears. In particular, a characteristic peak identified as the eucryptite crystalline phase disappears, whereas and the characteristic peak identified as the spodumene crystalline phase appears.

From these results, it can be predicted that in a reheat-treatment process that can be additionally performed by a user such as a dental laboratory or a dental hospital in the manufacture of a dental restoration, the bulk block according to the present invention will exhibit changes in physical properties such as strength even under specific conditions, and it will be necessary to set conditions in consideration of a change in the crystalline phase.

Such a crystalline phase constituting the bulk block according to the present disclosure can be formed in the form of microcrystals. These microcrystals exhibit various sizes and size distributions depending on temperature, thereby realizing various mechanical properties and light transmittances.

In addition, since the bulk block has a crystalline size gradient with respect to the depth thereof, the bulk block may realize gradient light transmittance and mechanical properties with respect to the depth. Moreover, since no interface exists at the point of change in the main crystalline size gradient value, machining through interlayer bonding is not necessary, and the problem of interlayer separation occurring during cutting may be solved. In addition, this functional grading makes it possible to provide an artificial tooth prosthesis with increased structural stability in terms of force dispersion.

In the bulk block according to the present invention, the crystalline size gradient may be sloped such that the lithium silicate-based crystalline phase has a mean grain size in the rage of 0.05 to 1.0 μm, and the eucryptite crystalline phase has a mean grain size in the range of 1.0 to 4.0 μm.

Figure 3:
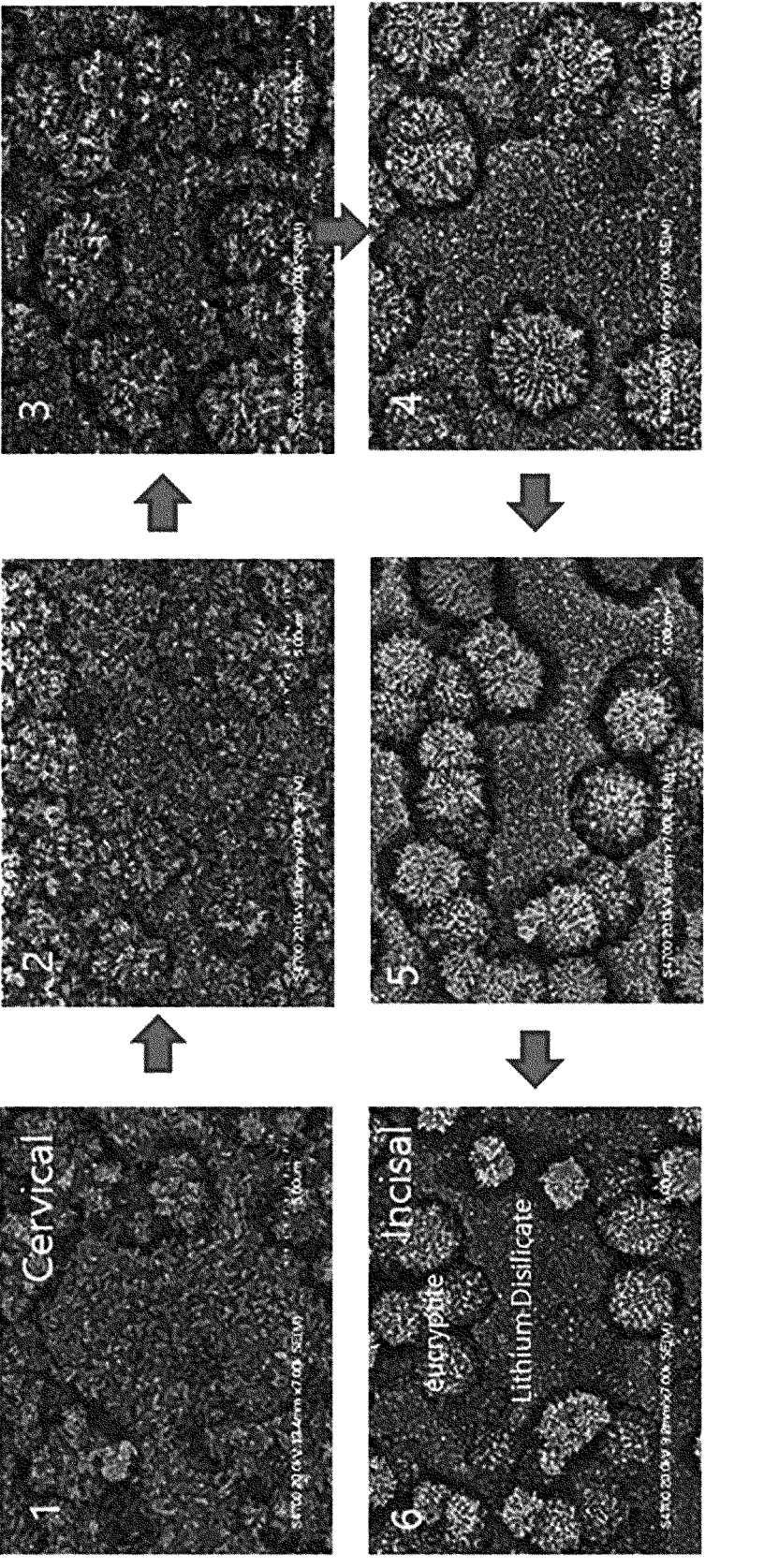
FIG. 3 illustrates scanning electron microscope (SEM) images of specimens obtained by slicing one bulk block according to an embodiment of the present invention by a thickness of 1.5 mm in a depth direction of the block, in which the depth direction is represented as a cervical to incisal direction in consideration of the use as a dental restoration.

As an example, FIG. 3 illustrates scanning electron microscope (SEM) images of the dental bulk block according to the present invention, illustrating six SEM images of specimens obtained by slicing one bulk block to a thickness of 1.5 mm. These SEM images are arranged in an order corresponding to the depth direction of the bulk block, and the depth direction is represented as a cervical to incisal direction of the tooth for convenience in consideration of application purpose. Specifically, a cut surface of each 1.5 mm thick specimen was observed by observing the SEM images in the direction from the SEM image of a top portion of the block (the portion corresponding to the cervical area) illustrated at the upper left side of FIG. 3 to the SEM image of a bottom portion of the block (the portion corresponding to the incisal area).

The SEM image thus obtained may be used to calculate a mean grain size of crystalline phases. Specifically, the mean grain size may be obtained by a linear intercept method involving: drawing a diagonal line or a straight line randomly on the SEM image; dividing by the length of the line the number of crystalline grains intercepted by the line; and determining the mean grain size depending on magnification.

In the previous and following descriptions, it will be understood that the size of the crystal phases is calculated by this method.

The bulk block according to the present disclosure is a functionally graded material. The functionally graded material is subjected to cutting machining such as CAD/CAM machining, under the same machining conditions. Therefore, considering the aspects of machinability, and light transmittance capable of being clinically usable in artificial tooth restoration materials, the lithium silicate-based crystalline phase preferably has a mean grain size in the range of 0.05 to 1.0 μm, and the eucryptite preferably has a mean grain size in the range of 1.0 to 4.0 μm. In particular, since eucryptite is a porous crystalline phase whose particle shape is a surface protrusion (dendrite), it can be predicted that this morphology will advantageously cause an increase in machinability.

The dental bulk block according to the present disclosure has the crystalline size gradient described above, and thus has a light transmittance gradient with respect to the depth thereof.

In particular, considering the range of the mean grain size in the above-described crystalline phase size gradient, the light transmittance gradient may be in the range of 25 to 45% based on a wavelength of 550 nm.

In the previous and following descriptions, the light transmittance is measured using a UV-visible spectrometer (UV-2401PC, Shimadzu, Japan).

As described above, in the dental bulk block according to the present disclosure, no interface exists at the point of change in the crystalline size gradient value. Therefore, in this aspect, it can be seen that the light transmittance gradient varies in the range of 0.5 mm in depth, and substantially varies in the range of 1.5 mm in depth.

Figure 4:
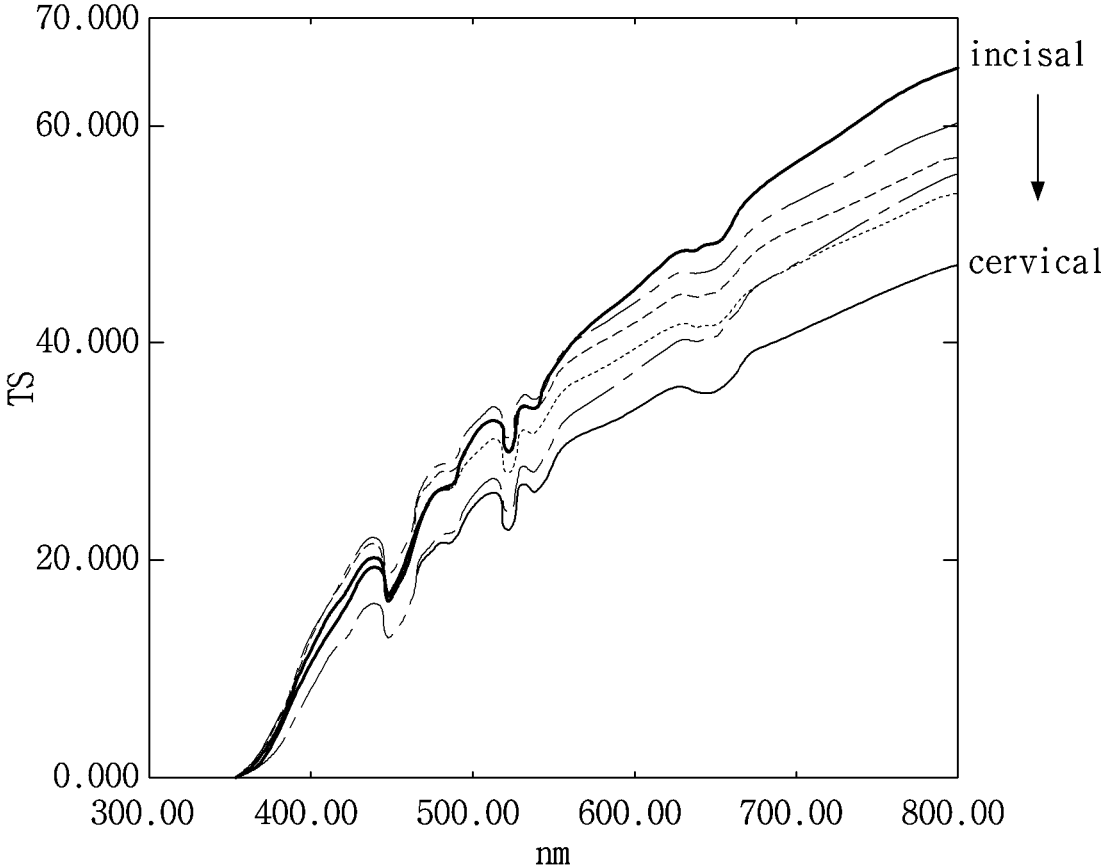
FIG. 4 illustrates a graph of a measurement result of visible light transmittance for 1.5 mm thick slice specimens of the bulk block according to the present disclosure.

In order to measure the light transmittance the dental bulk block according to the present disclosure for each gradient position, after cutting the block into specimens each with a thickness of about 1.5 mm in the depth direction where transparency decreases, the surfaces of the obtained specimens were wiped clean with ethanol, and then the light transmittance was measured using a UV-visible spectrometer (UV-2401PC, Shimadzu, Japan). Here, the measurement was performed under a condition in which the measurement wavelength range was 300 to 800 nm, and the slit width was 2.0 nm. It can be seen from the results of FIG. 4 that there is a difference in light transmittance between the 1.5 mm thick slice specimens.

These results are represented as spectra arranged from top to bottom in an order corresponding to an incisal to cervical direction so as to correspond to the specimens illustrated in the SEM images of FIG. 3.

In FIG. 3, each of the specimens corresponds to a specimen for each depth in Table 1 below.

TABLE 1

| Specimen No. | Depth (mm) |
|---|---|
| 1 | 1.5 |
| 2 | 3.0 |
| 3 | 4.5 |
| 4 | 6.0 |
| 5 | 7.5 |
| 6 | 9.0 |

This result is believed to indicate that the light transmittance varies even in the range of 1.5 mm in depth, i.e., a gradient light transmittance is exhibited in a range of 1.5 mm in thickness. This can be said to be a result clearly showing that the dental bulk block according to the present disclosure is a functionally graded material. In addition, when a prosthesis such as a crown is manufactured using the dental bulk block according to the present disclosure, the position of the block corresponding to a cusp of a tooth is machined to the largest thickness. Therefore, it can be predicted that aesthetically desirable light transmittance can be exhibited even in this thickness range.

In another aspect, the dental bulk block according to the present disclosure has a shade gradient and, specifically, has a gradient in L*, a*, and b* values measured by color difference analysis with respect to depth. As described above, in the dental bulk block according to the present disclosure, no interface exists at the point of change in the crystalline size gradient value. Therefore, in this aspect, it can be seen that the color difference value (ΔE) varies even in the range of 1.5 mm in depth.

The need for color standardization for accurate measurement, transmission, and reproduction of colors has led to inventing a color system. Various standardized color space systems have been developed, and the most widely used among them is the CIE L*a*b* color space (CIELAB color space) established by the Commission International de l'Eclairage (CIE) in 1976. Here, L* represents lightness, and a* and b* represent chromaticity coordinates. In the coordinates, L* represents a lighter color as the value increases and a darker color as the value decreases, and +a* means red, −a* means green, +b* means yellow, and −b* means blue.

In order to measure the color of the dental bulk block according to the present disclosure for each gradient position, cutting the block into specimens each with a thickness of about 1.5 mm in the depth direction where transparency decreases, the surface of the specimen was wiped clean with ethanol, and then the color was measured using a UV-visible spectrometer (UV-2401PC, Shimadzu, Japan). Here, the measurement was performed under a condition in which the measurement wavelength range was 380 to 780 nm, and the slit width was 2.0 nm. After setting a baseline using a reference sample, the reflectances of the specimens were measured to obtain an L*a*b* color system. For each of measured L*a*b* values, an average value obtained by repeating the measurement three times was used to reduce errors. Using these three values, ΔE, which represents the color difference, was obtained. When the ΔE of two specimens is 0, this means that no color difference exists, and when the ΔE thereof is 0 to 2, this means that the color difference is very slight. The ΔE of 2 to 4 means that the color difference is noticeable, and the ΔE of 4 to 6 means that the color difference is appreciable. The ΔE of 6 to 12 means that the color difference is much, and the ΔE of equal to or greater than 12 means that the color difference is very much.

In the case of the dental bulk block having the characteristics illustrated in FIGS. 1A to 3, it can be seen from the results in Table 2 below that the color difference value (ΔE) between the 1.5 mm thick slice specimens is 1.3 to 1.6. This result is believed to indicate that the color difference value (ΔE) varies even in the range of 1.5 mm in depth, i.e., a gradient shade with different colors is exhibited even in the range of 1.5 mm in depth. This can be said to be a result clearly showing that the dental bulk block according to the present disclosure is a functionally graded material in another aspect.

TABLE 2

| Specimen No. | Depth (mm) | L* | a* | b* | ΔE |
|---|---|---|---|---|---|
| 1 | 1.5 | 65.4 | −1.71 | 8.99 | |
| 2 | 3.0 | 66.9 | −1.79 | 9.51 | 1.58 |
| 3 | 4.5 | 68.2 | −1.89 | 10.11 | 1.43 |
| 4 | 6.0 | 70.1 | −1.99 | 11.10 | 2.14 |
| 5 | 7.5 | 69.8 | −2.21 | 9.82 | 1.33 |
| 6 | 9.0 | 68.5 | −2.45 | 10.54 | 1.50 |

In addition, the dental bulk block according to the present disclosure has a flexural strength gradient with respect to the depth thereof. In particular, considering the range of the mean grain size in the crystalline phase size gradient, the flexural strength gradient may be in the range of 220 to 350 MPa.

Meanwhile, considering machinability, and the aspect that it is possible to realize the functional grading of various physical properties as described above, the dental bulk block according to the present disclosure preferably has a crystallinity degree of 40 to 70%.

In the previous and following descriptions, the term "crystallinity degree" may be defined as the ratio of the crystalline phase to the amorphous glass matrix, which may be obtained through various methods. In one embodiment of the present disclosure, the crystallinity degree is a value automatically calculated by an X-ray diffractometer.

By manufacturing the dental bulk block according to the present disclosure using a glass-ceramic material in which a crystalline phase is precipitated in a continuous amorphous glass matrix, the dental bulk block including, as the crystalline phase, eucryptite and at least one selected from the group consisting of lithium metasilicate and lithium disilicate is obtained. The dental bulk block is a functionally graded material having the crystalline size gradient with respect to the depth thereof, and having no interface at the point of change in the crystalline size gradient value.

In particular, the crystalline phase preferably includes 40 to 60 vol. % of the lithium silicate-based crystalline phase, and 40 to 60 vol. % of the eucryptite crystalline phase, based on the total volume of the crystalline phases. When lithium phosphate is included as an additional crystalline phase, the amount thereof preferably does not exceed a maximum of 5 vol. %.

Generally, the amount of the crystalline phases may be calculated through X-ray diffraction analysis. For example, in a specimen having two polymorphs a and b, the ratio Fa of the crystalline phase a is quantitatively expressed by Equation 1 below.

$$F_a = \frac{1}{1 + K\left(\frac{I_b}{I_a}\right)} \qquad \text{(Equation 1)}$$

This value may be obtained by measuring the strength ratio of the two crystalline phases and obtaining the constant K. K is the absolute strength ratio $I_{0a}/I_{0b}$ of two pure polymorphs, which is obtained by measuring a standard material.

As described above, the eucryptite crystalline phase may serve to improve cutting machinability of the glass-ceramic including the lithium silicate-based crystalline phase. However, when the amount thereof is excessive, strength may be reduced. Therefore, in view of machinability and strength, the amount of eucryptite in the crystalline phase is preferably 40 to 60 vol. % based on the total volume of the crystalline phases.

In the previous and following descriptions, the term "continuous glass matrix" may be defined as a glass matrix in which an interlayer interface does not exist in the glass matrix and the composition constituting the glass matrix is uniform in the entire block.

Specifically, a preferred glass matrix may include 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$. Here, the molar ratio of $SiO_2/(Li_2O+Al_2O_3)$ may be 2.10 to 2.90.

In addition to the above main components, the glass matrix may further include 0.5 to 1.0 wt % of ZnO, 0.1 to 2.0 wt % of CaO, and 0.2 to 2.5 wt % of $Na_2O$.

In addition, the lithium silicate-based crystalline phase may be controlled depending on the molar ratio of $SiO_2$/ $Li_2O$. For example, when the molar ratio of $SiO_2$/$Li_2O$ is 2.20 to 2.59, the lithium disilicate crystalline phase and the lithium metasilicate crystalline phase may be precipitated together. On the other hand, when the molar ratio of $SiO_2$/ $Li_2O$ is 2.60 to 3.00, only the lithium disilicate crystalline phase may be precipitated.

When the molar ratio of $SiO_2$/$Li_2O$ exceeds 3.00, spodumene, orthoclase, petalite, virgilite, etc. containing a large amount of $SiO_2$ may be generated rather than eucryptite as the LAS-based crystalline phase together with lithium disilicate, which is undesirable.

This glass composition is subjected to crystal nucleation and crystal-growth heat treatment for crystallization to precipitate a crystalline phase in an amorphous glass matrix. In the case of the above-described glass matrix, the temperature at which a crystal nucleus starts to grow is 500 to 850° C. That is, the crystal nucleus starts to form from a minimum of 500° C. and a crystal grows while the temperature is raised. The crystal grows up to a maximum of 850° C. at which the lowest light transmittance is exhibited in artificial teeth. In other words, the light transmittance is gradually lowered from the temperature at which the crystal starts to grow to a maximum of 850° C. Therefore, if this crystal growth is realized in a single bulk block, this may be realized as a technique by which multi-gradation of natural teeth is imitated.

All natural teeth have various light transmittances. If such a change in light transmittance depending on the temperature of heat treatment is embodied in a single bulk block, the multi-gradation of natural teeth may be fully realized.

In this respect, the present disclosure provides a method of manufacturing a dental bulk block. The method includes the steps of: preparing a block having a predetermined shape by melting a glass composition including 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$, in which the molar ratio of $SiO_2$/$(Li_2O+Al_2O_3)$ is 2.10 to 2.90, followed by molding and cooling of the melted glass composition in a mold, followed by annealing from 480° C. down to 250° C. at a predetermined rate for a period of 20 minutes to 2 hours; and heat-treating the block in a gradient heat treatment furnace at a temperature in the range of 850 to 1,000° C. under a temperature gradient in a depth direction of the block.

As described above, in addition to the above main components, the glass matrix may further include 0.5 to 1.0 wt % of ZnO, 0.1 to 2.0 wt % of CaO, and 0.2 to 2.5 wt % of $Na_2O$.

In addition, the lithium silicate-based crystalline phase may be controlled depending on the molar ratio of $SiO_2$/ $Li_2O$. For example, when the molar ratio of $SiO_2$/$Li_2O$ is 2.20 to 2.59, the lithium disilicate crystalline phase and the lithium metasilicate crystalline phase may be precipitated together. On the other hand, when the molar ratio of $SiO_2$/ $Li_2O$ is 2.60 to 3.00, only the lithium disilicate crystalline phase may be precipitated.

When the molar ratio of $SiO_2$/$Li_2O$ exceeds 3.00, spodumene, orthoclase, petalite, virgilite, etc. containing a large amount of $SiO_2$ may be generated rather than eucryptite as the LAS-based crystalline phase together with lithium disilicate, which is undesirable.

In a preferred embodiment, the heat-treating the block in the gradient heat treatment furnace may be performed under conditions in which the temperature is raised to a maximum temperature at a fast temperature increase rate of 30 to 110° C./min, and when the temperature is raised to a maximum temperature of 850 to 1,000° C. is reached, the maximum temperature is maintained for a short period time of 1 to 5 minutes.

As the mobility of $SiO_2$ varies depending on the temperature increase rate, temperature, and holding time, various LAS-based crystalline phases may be precipitated, and machineability, etc. may vary depending on these crystalline phases. Therefore, a preferred LAS-based crystalline phase in satisfying machineability intended in the present invention may be eucryptite, and preferred heat treatment conditions for forming such a crystalline phase may be to allow the temperature to rapidly reach the maximum temperature and allow the maximum temperature to be maintained for a short period of time. That is, performing rapid heat treatment as a method of stopping the crystal growth of the LAS-based crystalline phases in an initial state may be critical in terms of generating eucryptite.

As described above, the glass composition exhibits a characteristic in which the light transmittance of the material depends on the range of temperature of heat treatment. Therefore, when heat treatment is uniformly applied to the entire block, constant light transmittance is exhibited. However, when heat treatment is applied to the block under the temperature gradient, multi-gradation of physical properties or light transmittance may be exhibited in a single block.

A bulk-type block is used as a workpiece for CAD/CAM machining. In the method according to the present disclosure, such a block is heat-treated by applying heat to the block under a temperature gradient in the depth direction, thereby obtaining a bulk block having light transmittance and strength with multi-gradation.

Controlling the light transmittance of conventional glass-ceramics is generally difficult due to coarse crystalline phases thereof, and machining thereof is difficult due to high strength thereof. On the contrary, in the case of the glass composition employed in the present disclosure, microcrystals can be formed, and these microcrystals exhibit various sizes and size distributions depending on temperature, thereby realizing various physical properties and light transmittances. In view of this, the block is manufactured using a single glass composition and then is heat-treated under a temperature gradient, thereby embodying multi-gradation of the mechanical properties and light transmittance of a single bulk block.

Here, the meaning "the step of heat-treating the block under the temperature gradient in the depth direction thereof" means that the temperature can be sequentially increased from a lower end to an upper end of the block in the depth direction thereof and that the temperature gradient is feasible with a partial temperature difference. The selection of the temperature gradient may depend on the characteristics of natural teeth of a patient who needs an artificial dental prosthesis or may depend on the unique characteristics of a portion of a tooth requiring the dental prosthesis.

However, considering typical natural teeth, the heat-treating is preferably performed under a temperature gradient in such a manner that the temperature is gradually increased from the lower end to the upper end of the block with respect to the depth thereof.

When the heat treatment method according to the present disclosure is performed using the above-described glass composition, it is possible to imitate the characteristic in which the light transmittance is low in the cervical area and is gradually increased toward the incisal area in the structure of natural teeth. This makes the method according to the present disclosure very economically advantageous because there is no need to characterize prostheses separately during manufacturing, unlike in a conventional method.

In addition, with respect to the physical properties of natural teeth, enamel, which is the surface layer, has high flexural strength, but dentin therein has low flexural strength, thereby absorbing and dispersing external forces. In the present disclosure, it is possible to obtain a functionally graded material having a mechanical property gradient, particularly a flexural strength gradient, depending on the depth of heat treatment due to the difference in microstructure. Therefore, it is possible to reproduce physical properties very similar to those of natural teeth.

Manufacturing a dental restoration using the dental bulk block obtained according to the present disclosure may be expected to significantly improve machinability. As a specific example, one embodiment of the present disclosure provides a method of manufacturing a dental restoration. The method includes the steps of manufacturing a predetermined dental restoration by machining the above-described dental bulk block using a machining machine-tool, and polishing or glazing the predetermined dental restoration.

In the previous and following descriptions, examples of the dental restoration include crowns, inlays, onlays, veneers, abutments, and the like.

Here, the glazing may be performed at 730 to 820° C. for 30 seconds to 10 minutes. This may be a conventional finishing heat treatment process in which there is little change in light transmittance due to heat treatment. In general, glazing is performed within a range that does not change inherent light transmittance of bulk blocks. During glazing heat treatment, strength may be increased by equal to or greater while surface microcracks are alleviated (surface healing).

When the holding time exceeds 20 minutes, spodumene or virgilite crystals with an increased $SiO_2$ amount may be generated. Thus, when such a phase transformation is not intended, the glazing is preferably performed at 730 to 820° C. for 30 seconds to 10 minutes.

Figure 8A:
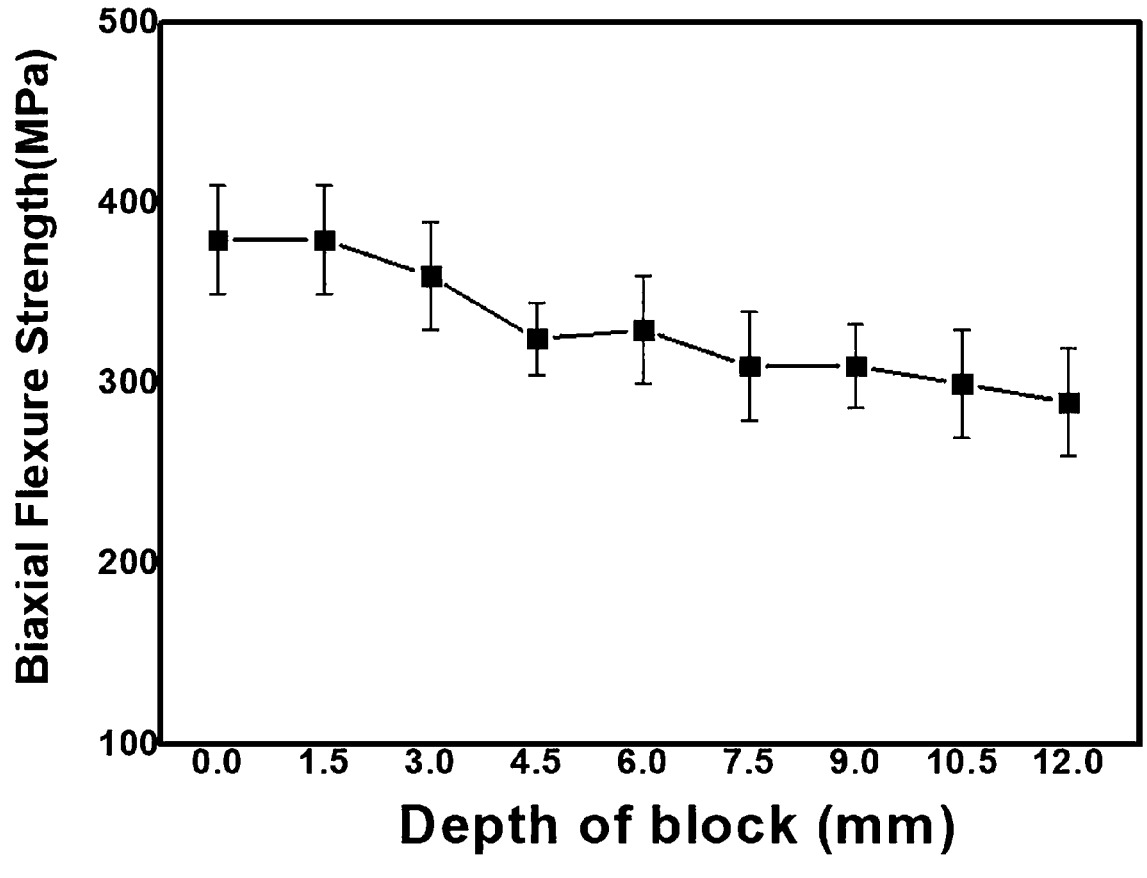

Due to the microcrack alleviation effect through the glazing under these conditions, the dental restoration may have a biaxial flexural strength gradient of 300 to 380 MPa, which can be confirmed from the results of FIG. 8A.

However, in a specific embodiment of the method of manufacturing the dental restoration using the bulk block according to the present disclosure, the glazing may be performed to control light transmittance of the machined dental restoration through heat treatment at a temperature of at least 825° C. That is, after machining the bulk block to manufacture the dental restoration, the glazing may be used for the purpose of controlling brightness by reducing the translucency in the final finishing step.

In manufacturing a dental restoration by machining a bulk block by a processor or a user, there may be cases in which the light transmittance is unintentionally changed to a high degree. In this case, for a conventional lithium disilicate-based bulk block, it is necessary to discard the machined bulk block, re-machine a bulk block that satisfies a desired light transmittance through a predetermined heat treatment, and then machine the bulk block into a dental restoration. However, the bulk block according to the present disclosure is a specific bulk block having a fine crystalline phase, and may exhibit a characteristic in which the light transmittance is controlled depending on the temperature of heat treatment. Therefore, re-machining is not necessary, and the light transmittance may be easily controlled again by performing the glazing under a predetermined condition during the process of finishing a machined workpiece to obtain a final dental restoration. Thereby, it is possible to simply cover a discolored tooth generated during machining of the workpiece into the dental restoration.

The glazing for this purpose is preferably performed at a temperature of at least 825° C. for 30 seconds to 10 minutes. When the holding time is prolonged, spodumene or virgilite crystals with an increased $SiO_2$ amount may be generated. Thus, when such a phase transformation is not intended, the glazing is preferably performed at a temperature of at least 825° C. for 30 seconds to 10 minutes.

Figure 8B:
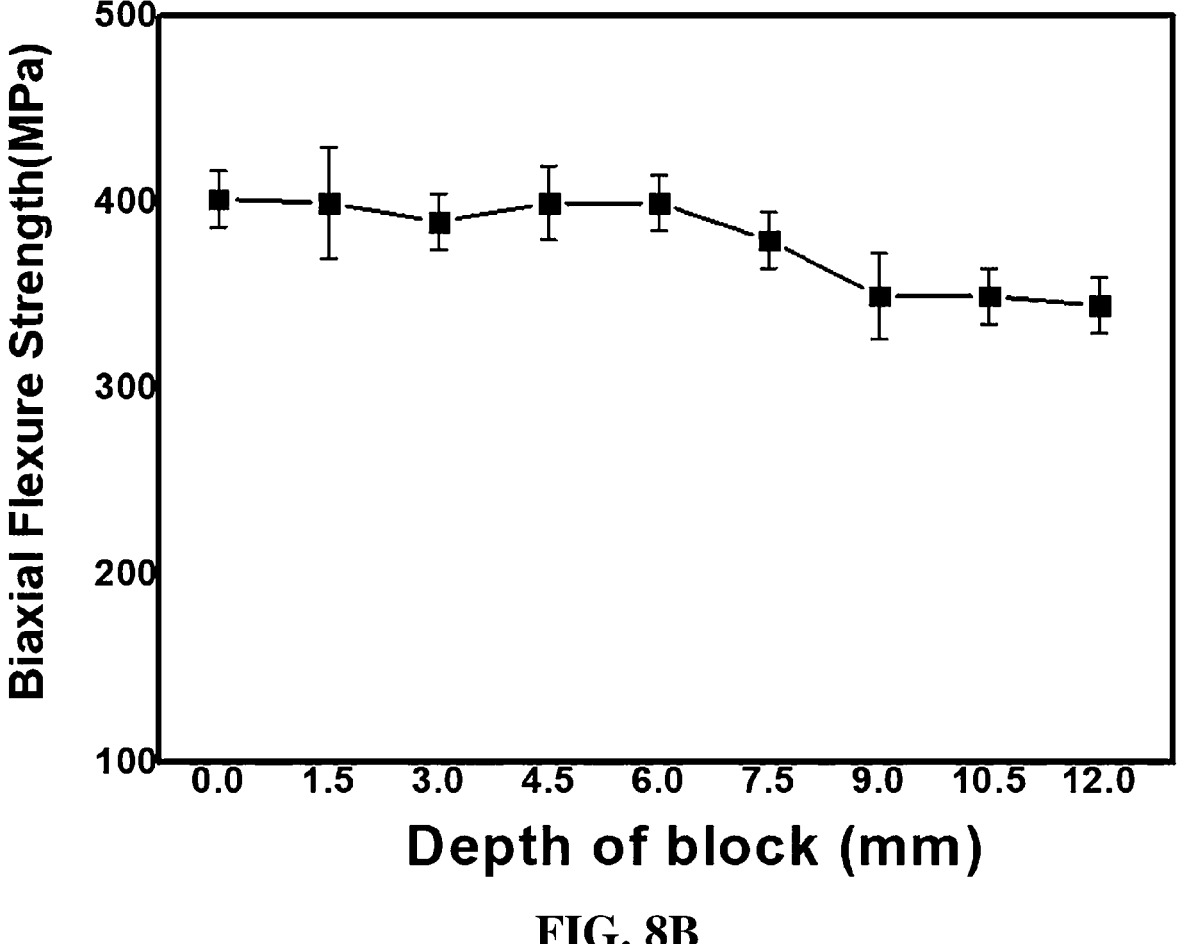

Due to crystal growth through the glazing under these conditions, the dental restoration may have a biaxial flexural strength gradient of 350 to 400 MPa, which can be confirmed from the results of FIG. 8B.

Characteristically, in the case of the dental bulk block obtained according to the present disclosure, it is possible to significantly lower the resistance generated in the machining machine-tool during machining. Specifically, a dental bulk block (this invention) having the characteristics as illustrated in FIGS. 1A to 3 and having dimensions of 12×14×18 mm was prepared. The dental bulk block was rotated at 250 RPM and was cut with an IsoMet™ low speed cutter (Buehler, Germany) and a diamond electroplated wheel (2514485H17, Norton, USA), and a cutting time was measured.

In addition, for each of a conventional lithium disilicate-based block (Rosetta SM, HASS Corp.), a zirconia reinforced lithium disilicate-based block (Celtra Duo, Dentsply-Siron), and an LAS reinforced lithium disilicate-based block (Nice, Straumann), a cutting time was measured in the same manner as described above.

From each cutting time value thus obtained, cutting resistance (%) was calculated. Specifically, based on 100% of the cutting time obtained for the conventional lithium disilicate-based bulk block, the cutting time for each of the bulk blocks was converted into a relative percentage thereto, and this was calculated as each cutting resistance value.

The results are illustrated in FIG. 5.

From the results of FIG. 5, it can be seen that the conventional lithium disilicate-based block had the highest cutting resistance, followed by the LAS reinforced lithium disilicate-based block and the zirconia-reinforced lithium disilicate-based block, and the block according to the present disclosure exhibited significantly low cutting resistance. Here, as the block according to the present invention, two types of blocks having molar ratios of $SiO_2/Li_2O$ (abbreviated as S/L) of 2.7 and 2.5, respectively, were used. Even when the lithium disilicate crystalline-phase was included, the cutting resistance was significantly low.

From these results, it can be predicted that the glass-ceramic block according to the present invention is the most machinable, which is due to the inclusion of eucryptite among the LAS-based crystalline phases.

In a specific embodiment of the present disclosure, a glass composition is prepared by weighing and mixing 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$, in which the molar ratio of $SiO_2/(Li_2O+Al_2O_3)$ is 2.10 to 2.90.

As a component of the glass composition, $Li_2CO_3$ may be added instead of $Li_2O$. In this case, carbon dioxide ($CO_2$), which is a carbon (C) component of $Li_2CO_3$, is exhausted in a gas form during glass melting. In addition, as alkali oxides, $K_2CO_3$ and $Na_2CO_3$ may be added instead of $K_2O$ and $Na_2O$, respectively. In this case, carbon dioxide ($CO_2$), which is a carbon (C) component of $K_2CO_3$ and $Na_2CO_3$, is exhausted in a gas form during glass melting.

The mixing is performed using a dry mixing process. Examples of the dry mixing process includes a ball-milling process or the like. Specifically, the ball-milling process involves charging a starting raw material into a ball-milling machine, and then rotating the starting the material at a predetermined speed to mechanically pulverize and uniformly mix the starting raw material. Balls for use in the ball-milling machine may be balls made of a ceramic material such as zirconia or alumina. The balls may have the same sizes, or at least two different sizes. The sizes of the balls, milling time, rotation speed of the ball milling machine, etc. are controlled in consideration of a desired grain size. For example, in consideration of the grain size, the size of each of the balls may be set to be in the range of about 1 to 30 mm, and the rotation speed of the ball milling machine may be set to be in the range of about 50 to 500 RPM. The ball milling is preferably performed for 1 to 48 hours in consideration of the desired grain size. During the ball milling, the starting raw material is pulverized into fine grains with a uniform grain size, and at the same time is uniformly mixed.

The mixed starting raw material is placed in a melting furnace, and the starting raw material is melted by heating the melting furnace containing the starting raw material therein. Here, the term "melting" means that the starting raw material is converted into a viscous liquid state, not a solid state. The melting furnace is preferably made of a material having a high melting point and a high strength and also having a low contact angle for suppressing the phenomenon in which a molten material is adhered thereto. To this end, preferably, the melting furnace is made of a material such as platinum (Pt), diamond-like carbon (DLC), or chamotte, or is coated with a material such as platinum (Pt) or diamond-like carbon (DLC).

The melting is preferably performed at 1,400 to 2,000° C. under normal pressure for 1 to 12 hours. When a melting temperature is less than 1,400° C., the starting raw material may fail to melt. On the other hand, when the melting temperature exceeds 2,000° C., excessive energy consumption is necessary, which is not economical. In addition, when a melting time is very short, the starting raw material may fail to sufficiently melt. On the other hand, when the melting time is very long, excessive energy consumption is necessary, which is not economical. The temperature increase rate of the melting furnace is preferably about 5 to 50° C./min. When the temperature increase rate of the melting furnace is very slow, a long period of time may be taken, which may reduce productivity. On the other hand, when the temperature increase rate thereof is very fast, a rapid temperature increase may cause an increase in volatilization amount of the starting raw material, and the physical properties of glass-ceramic may be poor. The melting is preferably performed in an oxidation atmosphere such as oxygen ($O_2$) and air.

The molten material is poured into a defined mold in order to obtain a dental glass-ceramic having a desired shape and size. The mold is preferably made of a material having a high melting point and a high strength and also having a low contact angle for suppressing the phenomenon in which the glass molten material is adhered thereto. To this end, the mold is made of a material such as graphite and carbon. In order to prevent thermal shock, the molten material is preferably preheated to 200 to 300° C. and then be poured into the mold.

After the molten material contained in the mold is formed and cooled, the resultant material is preferably subjected to annealing at a predetermined rate from 480 to 250° C. for 20 minutes to 2 hours. With the annealing, it is possible to reduce stress deviation in a formed product, preferably so that no stress exists, thereby having a desirable effect on controlling the size of the crystalline phase and improving the homogeneity of crystal distribution in a subsequent crystallization process. Therefore, it is possible to ultimately obtain a desired functionally graded material.

Here, the predetermined rate is preferably 2.3 to 14° C./min in terms of achieving sufficient annealing.

The formed product subjected to the annealing is transferred to a firing furnace for crystallization heat treatment to perform crystal nucleation and growth, thereby manufacturing a desired glass-ceramic.

FIG. 6 is a mimetic diagram illustrating a method of performing crystallization heat treatment under a temperature gradient according to the present disclosure. In the crystallization heat treatment of a block-type or ingot-type bulk block, the heat treatment is performed under a temperature gradient in a depth direction so that an upper end of the block is heat-treated at high temperature and a lower end thereof is heat-treated at low temperature.

In the previous and following descriptions, the step of performing the heat treatment under the temperature gradient is not limited to any specific apparatus or method. For example, the heat treatment may be performed in a gradient heat treatment furnace, the operating temperature may be set to 850 to 1,000° C., the temperature increase rate may be set to 30 to 110° C./min, and the holding time may be set to 1 to 5 minutes.

With the heat treatment under the temperature gradient, the bulk block exhibits a light transmittance gradient in which the light transmittance becomes high from the high-temperature heat-treated upper end toward the low-temperature heat-treated lower end, and has a flexural strength gradient in which the flexural strength becomes low from the upper end toward the lower end. This is because the size of crystals in the glass-ceramic can be controlled depending on the temperature. The crystalline phase generated through the heat treatment under the temperature gradient includes eucryptite and a lithium silicate-based crystalline phase such as lithium metasilicate or lithium disilicate. Thus, the bulk block is manufactured in the form of a functionally graded material in which the lithium silicate-based crystalline phase has a mean grain size in the range of 0.05 to 1.0 μm, and the eucryptite crystalline phase has a mean grain size in the range of 1.0 to 4.0 μm.

Figure 7:
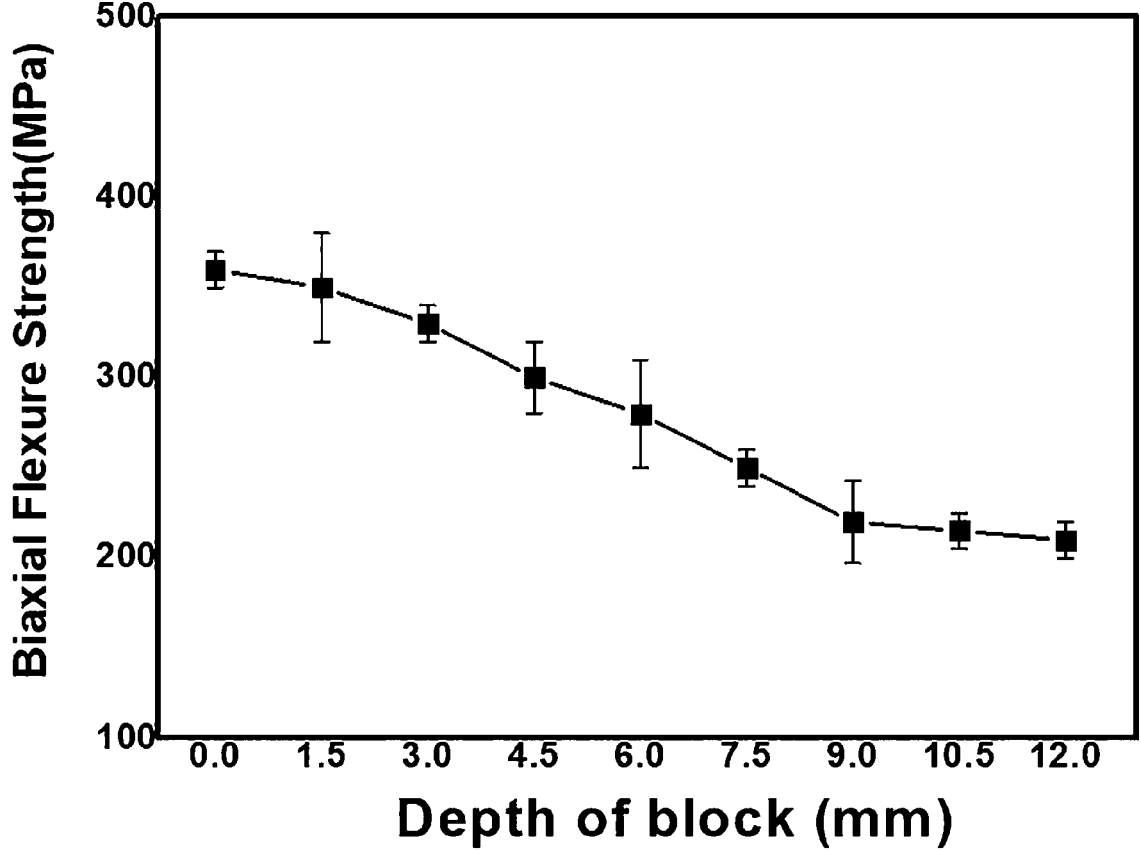
FIG. 7 is a graph illustrating a change in biaxial flexure strength as a function of the depth of the bulk block according to the embodiment of the present invention.

In addition, for the bulk block obtained according to the present disclosure, the change in flexural strength with respect to the depth of the bulk block was measured, and the results are illustrated in FIG. 7.

For the bulk block subjected to glazing at 820° C. for 2 minutes, the flexural strength was measured, and the results are illustrated in FIG. 8A.

For the bulk block subjected to glazing at 840° C. for 2 minutes, the flexural strength was measured, and the results are illustrated in FIG. 8B.

Although the exemplary embodiments of the present disclosure have been disclosed for illustrative purposes, those skilled in the art will appreciate that various modifications, additions, and substitutions are possible, without departing from the scope and spirit of the disclosure as disclosed in the accompanying claims.

What is claimed is:

1. A dental bulk block comprising a crystalline phase in an amorphous glass matrix, wherein:

the crystalline phase comprises at least one lithium silicate-based crystalline phase selected from the group consisting of lithium metasilicate and lithium disilicate, and a eucryptite crystalline phase;

the dental bulk block is a functionally graded material having a crystalline size gradient with respect to a depth thereof and no interface at a point of change in a main crystalline size gradient value;

when the dental bulk block is heat-treated at 820° C. for 40 minutes, the dental bulk block exhibits a characteristic peak of a spodumene crystalline phase in an X-ray diffraction analysis result graph; and when the dental bulk block is heat-treated at 820° C. for 2 minutes, the dental bulk block does not exhibit a characteristic peak of a spodumene crystalline phase in the X-ray diffraction analysis result graph, and wherein the crystalline size gradient is sloped such that the at least one lithium silicate-based crystalline phase has a mean grain size in a range of 0.05 to 1.0 $\mu m$, and the eucryptite crystalline phase has a mean grain size in a range of 1.0 to 4.0 $\mu m$, and wherein the amorphous glass matrix comprises 63.0 to 74.0 wt % of $SiO_2$, 11.0 to 13.7 wt % of $Li_2O$, 6 to 9 wt % of $Al_2O_3$, 1.5 to 3.5 wt % of $K_2O$, and 2.0 to 4.0 wt % of $P_2O_5$, and wherein a molar ratio of $SiO_2/(Li_2O+Al_2O_3)$ is 2.10 to 2.90.

2. The dental bulk block of claim 1, wherein the dental bulk block has a light transmittance gradient with respect to the depth of the dental bulk block, the light transmittance gradient throughout the entire gradient is in a range of 25 to 40% based on a wavelength of 550 nm, and the light transmittance gradient varies in a range of 0.5 mm in depth.

3. The dental bulk block of claim 1, wherein the dental bulk block has a gradient in L*, a*, and b* values measured by color difference analysis, and a color difference value ($\Delta E$) varies within a range of 1.5 mm in depth.

4. The dental bulk block of claim 1, wherein the dental bulk block has a crystallinity degree of 40 to 70%, wherein the crystallinity degree is a ratio of the crystalline phase to the amorphous glass matrix as calculated by the X-ray diffraction analysis.

5. The dental bulk block of claim 1, wherein the at least one lithium silicate-based crystalline phase and the eucryptite crystalline phase, in a combined volume, comprise 80 to 100 vol. % of the total crystalline phase, and each of the at least one lithium silicate-based crystalline phase and the eucryptite crystalline phase respectively comprises 40 to 60 vol. % of the total crystalline phase.

6. The dental bulk block of claim 1, wherein the dental bulk block has a flexural strength gradient with respect to the depth thereof, and the flexural strength gradient is in a range of 220 to 350 MPa throughout the entire flexural strength gradient.

7. The dental bulk block of claim 1, wherein a molar ratio of $SiO_2/Li_2O$ in the amorphous glass matrix is 2.20 to 2.59.

8. The dental bulk block of claim 1, wherein a molar ratio of $SiO_2/Li_2O$ in the amorphous glass matrix is 2.60 to 3.00.

* * * * *